United States Patent [19]

Chen et al.

[11] Patent Number: 5,384,264
[45] Date of Patent: Jan. 24, 1995

[54] METHOD AND APPARATUS FOR SINGLE STEP ASSAYS OF LIGAND-CONTAINING FLUIDS

[75] Inventors: Ted M. Chen, Chino; Yi-Ping Wang, Escondido, both of Calif.

[73] Assignee: Syntron Bioresearch, Inc., Vista, Calif.

[21] Appl. No.: 972,378

[22] Filed: Nov. 5, 1992

[51] Int. Cl.⁶ ............... G01N 33/543; G01N 33/552; G01N 33/558
[52] U.S. Cl. .................... 436/525; 422/56; 422/57; 422/58; 435/7.92; 435/7.94; 435/805; 435/970; 436/164; 436/169; 436/172; 436/510; 436/514; 436/524; 436/527; 436/805; 436/808; 436/810; 436/814; 436/818
[58] Field of Search ................... 422/56–58; 435/7.9, 7.92, 7.94, 805, 970; 436/164, 169, 172, 510, 514, 525, 524, 527, 805, 808, 810, 814, 818

[56] References Cited

U.S. PATENT DOCUMENTS

| | | | |
|---|---|---|---|
| 4,874,691 | 10/1989 | Chandler | 422/58 |
| 4,943,522 | 7/1990 | Eisinger et al. | 422/58 |
| 4,956,302 | 9/1990 | Gordon et al. | 422/58 |
| 5,145,789 | 9/1992 | Corti et al. | 436/810 |

FOREIGN PATENT DOCUMENTS 2204398 11/1988 United Kingdom ............... 435/970

*Primary Examiner*—Toni R. Scheiner
*Assistant Examiner*—Christopher L. Chin
*Attorney, Agent, or Firm*—Spensley Horn Jubas & Lubitz

[57] ABSTRACT

A method and apparatus for performing assays in a single step which does not require the user to perform a washing step, does not require the user to add any reagent or other solution other than analyte sample fluid to the apparatus, and does not require the user to come into contact with the apparatus at any point during the assay procedure after the fluid suspected of containing a particular ligand is added to the apparatus. The apparatus for performing the assay consists of a single container with at least three ports disposed through different planes in the body of the apparatus beneath which labelled antiligand (the first port), unlabelled antiligand (the second port), and unlabelled ligand (the third port) are disposed. Said labelled antiligand is complementary to both the analyte of interest and the unlabelled ligand, the latter of which serves as a control display for comparison of any color changes mediated by the label visible through the second port. The antiligands and ligands disposed beneath each port are bound to separate membranes. At least the first membrane is bibulous and is disposed at one end of a ramp where, at the top of which, it overlaps the second membrane thus slowing the flow of sample and improving the performance of the assay.

18 Claims, 2 Drawing Sheets

METHOD AND APPARATUS FOR SINGLE STEP ASSAYS OF LIGAND-CONTAINING FLUIDS

BACKGROUND OF THE INVENTION

1. Field of Invention

This invention relates to one-step methods for conducting assays of fluids suspected of containing selected ligands. It further relates to an apparatus for conducting these assays.

2. Description of the Prior Art

In recent years, immunoassay procedures have undergone nearly continuous refinement in an effort to simplify and speed the process of detecting selected ligands in fluids suspected of containing them (these fluids will hereafter be referred to as analyte samples). As a result of this work, assays using monoclonal antibodies which recognize different epitopic sites on an antigen have been developed which made it possible to conduct simultaneous assays without repeated incubation and washing of bound antibody.

One example of such a process can be found in U.S. Pat. No. 4,632,901. In the method of that patent, a liquid sample suspected of containing an antigen of interest is poured onto a porous material to which an antibody capable of binding the antigen of interest is coupled. Through capillary action of an absorbent material in contact with the porous material, the sample is drawn in a directed fashion through the porous material and past the coupled antibody. Antigen in the sample will be captured by, and will bind with, the coupled antibody.

After this first step is completed, a second step is taken wherein a separate solution of labelled antibody is passed through the porous material so as to bind to the antigens which are now bound to coupled antibody. Unbound labelled antibody is then flushed from the porous member by a washing step, which may be followed by an incubation period. Finally, a third solution containing substrate reactive with the label on the antibody of the second solution is added to cause a visible color change indicative of the presence of the antigen of interest. To facilitate accurate performance of this method, an apparatus is provided which funnels sample through to the absorbent member which, by capillary action, will pull the sample through the device and, in one embodiment, out of its bottom.

Similar to the three step method of U.S. Pat. No. 4,632,901 is the dipstick method of U.S. Pat. No. 4,366,241. In the dipstick method, the assay device is a strip on which an immunological ligand is bound. The strip is dipped into or otherwise contacted with the analyte sample, then successively contacted one or more separate solutions which may contain a labelled antiligand, enzyme substrate (for enzyme labels) and/or washing fluids to remove any unbound label. A filtration step may also be taken to facilitate complete washing (see, e.g., U.S. Pat. No. 4,623,461). Other researchers have suggested the use of a second control assay for verification of the assay results (see, e.g., U.S. Pat. No. 4,200,690 [method provided for analyzing fecal samples using two washing and incubating steps]).

For a similar dipstick device with both labelled and unlabeled antibody bound to the sample-receiving porous material (see PCT Application No. PCT/GB88/0322).

While the developments described above have provided compact, relatively efficient means for performing assays, several problems with the presently known procedures remain. First, after addition of the analyte sample to the assay device, these procedures require the addition or use of one or more additional solutions to complete the assay. As each solution is added to the device, or each device dipped into successive solutions, the opportunities for spillage or contact between the solution(s) and the user are enhanced. This problem is further worsened in assays which require the user to remove a portion of the device (such as a viewing port) during the procedure.

Multiple dipping or pouring steps present not only a possible loss of sensitivity of the assay (through loss of reagent solutions), but also an aesthetic and hygienic problem for the analyst. Consumers in particular are likely to be intimidated by the need to mix and add one or more solutions during the procedure, if not put-off altogether by the prospect of contacting the analyte sample (which is usually urine in consumer assays such as pregnancy tests).

Another consideration is how accurately the results of the assay are reported. Chromatographic devices are becoming more common in recent years. For example, U.S. Pat. Nos. 4,094,647, 4,235,601 and 4,361,537 describe test strip devices where different zones in the strip contain reagents needed to produce a detectable signal as analyte passes into or through the zones.

A variation on the strip devices described above requires the user to apply a second ligand containing fluid to the device after application of the analyte sample. A fluorescent or enzymatic label is covalently bound to the ligand in the second fluid; the ligand is specific to the analyte of interest and will bind thereto, allowing its detection on activation of the bound label. This and similar devices (see, e.g., U.S. Pat. No. 4,740,468) suffer to some extent from the same shortcoming as the devices which require washing and incubation steps; the need to use more than one solution at the correct time and in the correct order to perform the assay.

One effort to avoid the need for addition of reagent solutions found in prior art devices is reflected in U.S. Pat. No. 5,075,078. This patent describes several embodiments of chromatographic test strip devices which use a visually detectible result format generating plus (+) or minus (−) signs to indicate, respectively, the presence or absence of the analyte of interest in the sample.

In particular, the '078 devices are directed to solving the problem of "leading edge effects" i.e., where the plus or minus sign is not clearly or completely formed, causing the test results to be inconsistent or unreadable. To explain, conventional plus/minus assay devices include a chromatographic substrate of absorbent material. A test region will be located on the substrate, in which is located a procedural control bar parallel to the direction of fluid flow through the substrate and a patient test bar perpendicular to the control bar. Typically, a ligand specific to the analyte of interest will be bound within the test bar which will capture analyte present in the sample fluid. A label reagent is added to the device after addition of the analyte sample fluid; alternatively, the label reagent may be added with the sample fluid.

If the analyte of interest is present in the sample fluid, the label reagent will react with it in the test bar and with a corresponding ligand in the control bar, forming a plus sign. In absence of the analyte of interest, the label reagent will react only with the ligand bound in the control bar, forming a minus sign. However, experience with these prior art devices has shown that several failures can occur which produce misleading test results. For example, depletion of ligand in the control bar can prevent binding of label in that area, causing only part of the minus sign to appear. Another failure is caused by a solvent front which causes the edges of the control and/or test bars to become blurred; it is this phenomenon which is commonly referred to as a leading edge effect.

The plus/minus devices of the '078 patent attempt to avoid these failures by placing the control and test bars at a preferred 45° angle to the direction of fluid flow and at a 90° angle with respect to each other. A diffusible label application pad is included in the device which includes a label conjugated to a ligand (generally, an antibody). The device is described as being "self-performing" (i.e., requiring only the addition of analyte sample fluid to perform the test) and as producing clear test results (due to the orientation of the test and control bars, which is intended to minimize the distance the sample fluid must travel, thus limiting the opportunity for leading edge effects to affect the test results).

However, whether or not leading edge effects are controlled by the '078 patent's orientation of the control and test bars, the possibility for misleading results is still inherent in the device. Specifically, placement of the displays for positive and negative test results on the same region of the substrate by definition allows for the two results to be confused. Accordingly, a test device which provides for separate test result displays which cannot be confused is still needed in the art. Further, the device must still be user-friendly; i.e., require a minimum of steps to perform and allow those steps to be performed in a simple, hygienic manner. These needs are addressed by the present invention.

SUMMARY OF THE INVENTION

The present invention overcomes the limitations of prior assay procedures and devices and provides a method and device for performing simple, clean and accurate analyte assays.

These results are accomplished in the present invention by means summarized as follows:

The apparatus of the present invention comprises a closed container, preferably made of a nonporous plastic, such as the commercially available plastic "ABS" supplied by the Monsanto Company of St. Louis, Mo., in which a sample entry port and two display ports. The housing may be formed in two pieces, the first being a ported cover and the second being the floor, a portion of which is raised to form a membrane platform.

The sample entry port leads to a chamber in the housing in which a porous membrane having fibers therein of any orientation (preferably fiberglass) is disposed. The membrane extends upwardly out of the chamber, where it contacts a second porous membrane which is affixed to a platform extending substantially along the remaining length of the housing. At the end of the platform an absorbent pad may be present to collect excess sample fluid.

A soluble antiligand corresponding to the analyte of interest is coupled to the first porous membrane. This antiligand is conjugated to a label, preferably a metal label and most preferably colloidal gold. A second immobilized antiligand corresponding to the analyte of interest is coupled to the second porous membrane and positioned beneath the first of the two display ports. An immobilized ligand corresponding to the first antiligand is coupled to the second membrane and positioned apart from the second antiligand and beneath the second of the two display ports. The first soluble antiligand serves as a label reagent; the second immobilized antiligand serves as a patient test region, and the immobilized ligand serves as a procedural control region.

The assay is performed in a single step. An amount of analyte sample is dropped or poured into the sample port. All or most of the sample proceeds by capillary action (i.e., wicking) to the second port, thereby contacting and dissolving the first labelled antiligand along the way. If analyte is present in the sample, it will bind to an epitopic site on the labelled antiligand and pass therewith to the second membrane. The tightly fitted housing cover is adapted to retain all sample in the device, thus avoiding spillage and the need for any further contact between the sample and user.

The analyte sample fluid containing either labelled antiligand alone or a labelled antiligand/analyte complex (i.e., "first conjugate") will ascend by wicking up to the second membrane and along the latter to the patient test region beneath the first display bar. A first conjugate is present in the analyte sample fluid, the analyte therein will bind to an epitopic site on the immobilized second ligand, causing a reaction visible through the first display port.

For comparison, the analyte sample fluid will continue its migration along the second membrane past the first display port to the control bar beneath second display port. The labelled antiligand, conjugated or otherwise, will bind to the immobilized ligand present beneath in the control region, causing a visible reaction. If a reaction appears through the first display port which matches the reaction visible through the second, the test is positive for presence of analyte. If there is no reaction visible through the first port comparable in appearance to the control region, the test is negative for presence of analyte. If visible results appear through both display ports which are substantially dissimilar in appearance, the user is alerted that the test results are compromised and that the test should be repeated.

Several features of the inventive assay device assist in avoiding the latter set of test results. First, simultaneous migration of an excessive amount of analyte sample fluid is limited by requiring the fluid to ascend through the first membrane. If visible results appear through both display ports which are substantially dissimilar in appearance, the user is alerted that the test results are compromised and that the test should be repeated.

Second the impact of leading edge effects or depletion of bound antiligands or labels are minimized by physically separating the test and control regions and by using the presence of a reaction, rather than the appearance of a given shape, to signify a positive or negative result. Finally, the entire process is simplified by having the label reagent bound to a substrate placed within the device, thus avoiding any need to for the user to add a reagent or mix it with the analyte sample.

DESCRIPTION OF THE PREFERRED EMBODIMENTS

1. Definitions

For ease of understanding, the following definitions will apply throughout this description:

a) Ligand

A molecule or compound having one or more epitopic sites; i.e., those points at which another molecule or compound will bind. Ligands for purposes of this invention may include luteinizing hormone or other naturally occurring biological ligands in serum, plasma, urine or other fluids, and will preferably include antigens.

b) Antiligand

Receptor molecules or compounds which bind to particular epitopic sites on ligands. Antiligands may in this context include any naturally occurring or prepared biological receptor, and will preferably include antibodies.

For simplicity, the terms antibody and antigen will be used throughout this disclosure. It will be appreciated by those skilled in the art, however, that the invention is not limited to use with antigens and antibodies.

c) Analyte Sample

A liquid suspected of containing ligands of interest for which a particular assay will be specific.

d) Label

A molecule or compound which directly or indirectly mediates the production of a signal (such as a color change) which is used in assay procedures to indicate the presence or absence of ligands of interest in an analyte sample. Labels may include enzymes, fluorecsors and will preferably include metal sols.

e) Metal Label

Labels of metal sols; i.e., metal or metal compounds such as metal oxides, metal hydroxides, metal salts or polymer nuclei coated with a metal or metal compound. These metal labels may include dry forms of any of the above-named metals or metal compounds, and will preferably include colloidal gold in dry form.

f) Conjugate

Depending on the context in which it is used, "conjugate" shall mean a analyte labelled antiligand molecule first produced in the assay ("first conjugate") or the analyte labelled antiligand/unlabelled antiligand molecule produced second in the assay method ("second conjugate").

2. Preferred Embodiments

Apparatus: The Assay Device

Figure 1:
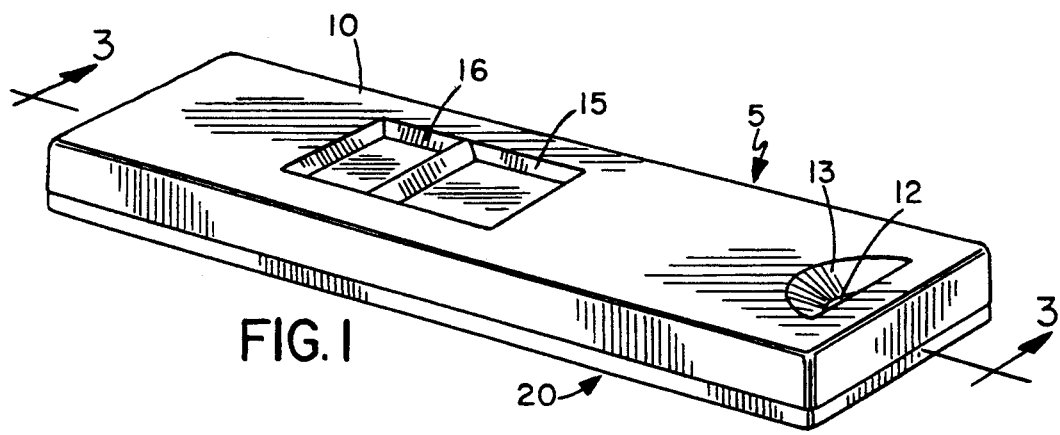
FIG. 1 is a perspective view of the assay unit.

Turning to FIG. 1, there is shown a perspective view of an apparatus which can be used to perform assays in accord with the invention. FIG. 1 therefore depicts a housing 5 of rectangular shape (although any appropriate shape may be employed). Housing 5 is composed of two parts. The first is housing cover 10 in which three openings appear. The first opening is sample entry port 12, which preferably has sloping walls 13 defining a full or half funnel extending downwardly toward the bottom surface 22 of housing floor 20 (see, FIG. 2) As shown in FIG. 3 (a view taken along line 3—3 of FIG. 1, walls 13 will preferably stop short of touching bottom surface 22 by a distance sufficient for a porous membrane described to it between them.

The second and third opening through housing cover 10 each form a separate display port through which the test result can be viewed and compared to a control display. To this end, the first display port 15 and second display port 16 are preferably side by side for ease of comparison.

Figure 2:
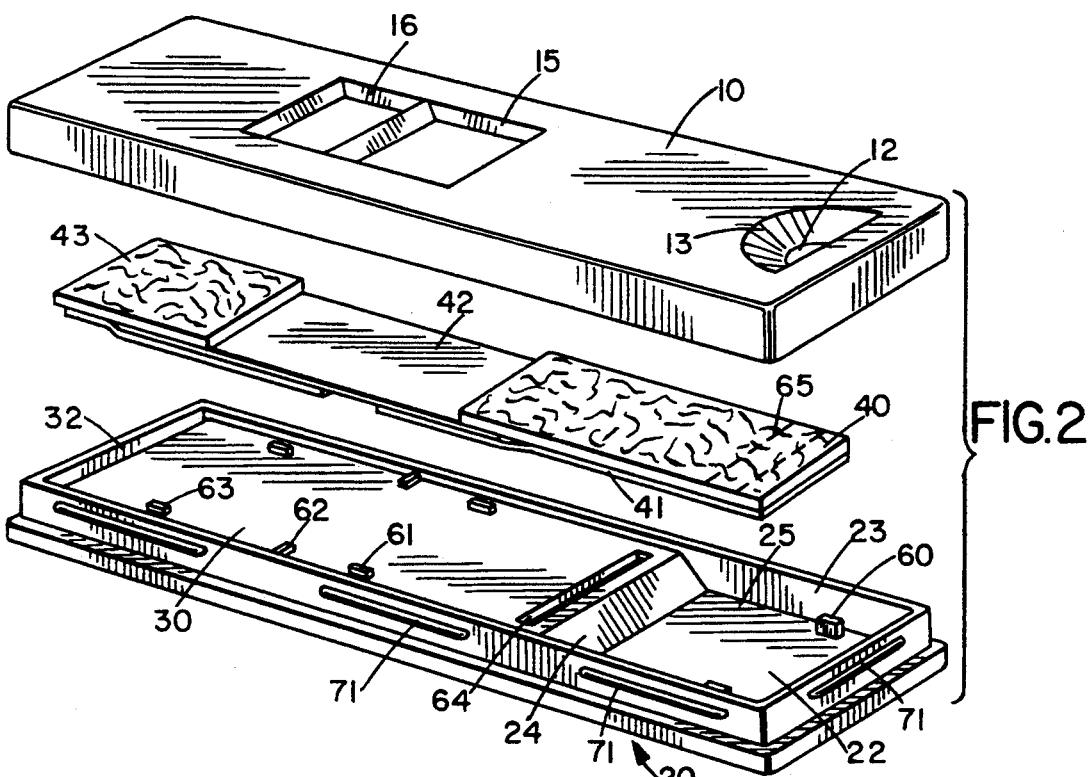
FIG. 2 is an exploded view of the components of the assay unit.
Figure 3:
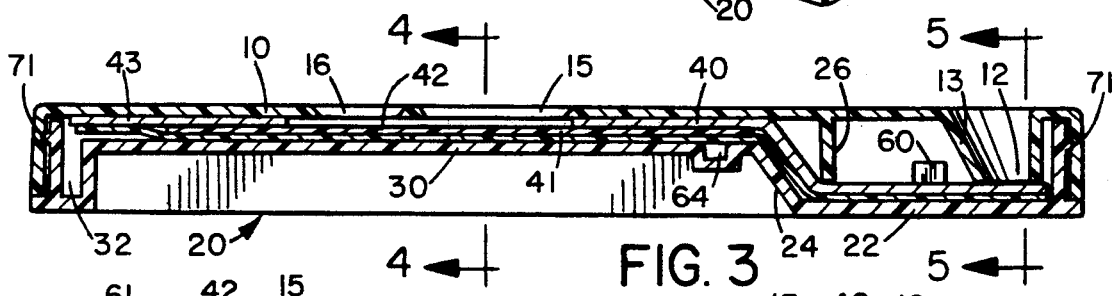
FIG. 3 is an enlarged sectional view taken on line 3—3 of FIG. 1.
Figure 5:
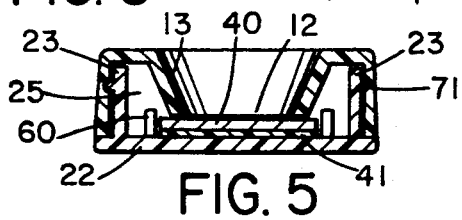
FIG. 5 is a sectional view taken on line 5—5 of FIG. 3.

Turning to FIG. 2, the apparatus is shown in exploded view. In this view, it can be seen that housing floor 20 is divided into two distinct regions. The first is depression 25, which is defined by bottom surface 22, sidewalls 23 and slope 24. In a preferred embodiment (shown in FIG. 3), housing cover 5 will have a vertical bar 26 extending downwardly into depression 25 just in front of slope 24 to hold membrane 40 (described below) in place. The second region of housing floor 20 begins at the top of slope 24 and consists of an extended surface forming platform 30 parallel to and extending away from depression 25 as shown in FIG. 2, fluid gully 64 may be included as a sink for excess analyte sample. Platform 30 may extend the length of housing floor 20 from slope 24, or it may stop just short of the end of housing floor 20, leaving room for fluid gulley 32 to collect excess analyte sample fluid (in the same manner as fluid gulley 64 see, FIG. 5).

Contained within housing 5 will be first and second porous membranes 40 and 42. Preferably, an absorbent pad 43 for collection of excess analyte sample fluid will also be included. The preferred spatial relationship of these membranes are shown in FIG. 2 as follows:

First porous membrane 40 will be disposed within depression 25 and along slope 24 to platform 30. Preferably membrane 40 will be affixed to a nonporous substrate 41 such as coated paper by an adhesive or other suitable means. Substrate 41 will extend along platform 30 to form a surface to which second porous membrane 42 will be affixed. First porous membrane 40 and 42 will be in contact with, but need not be affixed, to the other. In the most preferred embodiment, membrane 40 will be split at its point of attachment to substrate 41 to extend above and below the substrate. This configuration serves to regulate the flow of analyte sample from membrane 40 to membrane 42. Flow control can also be enhanced by placement of a well 64 below the junction between membranes 40 and 42.

In a preferred embodiment of the device, locating points will be present in depression 25 and platform 30 (examples of these points are representatively shown in FIG. 2 as points 60 through 63). These locating points respectively identify where the ligands described below will be bound to membranes 40 and 42. When the membranes are properly aligned along the locating points, the bound ligands and antiligands will be placed beneath the various ports through housing cover 5 as follows:

At the point on first porous membrane 40 corresponding to locating points 60, a first soluble antiligand, preferably an antibody and most preferably an antibody to human chorionic gonadotropin (i.e., anti $\beta$-hCG) will be bound so as to be beneath sample entry port 12. The preferred material for the first porous membrane is a fiberglass product such as that which is marketed under the trade names "MANNIWEB" or "MANNIGLAS" by Lydall, Inc. Binding will be by use of soluble aminosilanes. Other suitable materials include polyethylene or nitrocellulose pads and strips; means for binding ligands to these materials are well-known in the art.

The first soluble antiligand will be labelled according to means known in the art. For purposes of producing a clearly visible reaction, labels of metal sols are preferred, with labels of colloidal gold or selenium being most preferred. An example of a suitable product is colloidal gold available from Janssen Life Sciences Products. These colloidal metals will produce colored reactions without addition of further reagents; however, flourescors (such as fluorescein and phycobiliprotein) and enzymes (such as those identified in U.S. Pat. No. 4,275,149, incorporated to that extent herein, may also be used. To maximize contact of analyte sample with labelled antiligand, the latter should be bound to the membrane across its face; i.e., from one side to the other (see, bar 65 shown in phantom on FIG. 2).

The second immovable antiligand will be bound to the second porous membrane in a position corresponding to locating point 61. This will be the location of the patient test region, which is aligned beneath display port 15 in the assembled test device. Second porous membrane 42 will preferably be a chromatographic strip coated with gelatin to enhance the life of the strip and clarity of any visible reactions produced in the test. The second antiligand may be immovably attached to membrane 42 by means known in the art, including covalent bonding or attachment to an insoluble protein-coated surface (see, e.g., U.S. Pat. No. 4,200,690, the disclosure of which is to that extent herein incorporated).

Preferably, the second immovable antiligand will be bound in a bar or oval shape extending from side to side of the membrane 42 in a manner similar to the attachment of the first soluble antiligand to membrane 40. Use of a simple, unidirectional configuration such as a bar avoids the need for the user to determine if a more complex shape (such as a "+" or a "−") has been sufficiently formed to indicate a particular result. Further, use of a simple shape overcomes the impact of leading edge effects by making test results dependent on the appearance through the appropriate port of any shape or color, rather than of the appearance of a particular shape or color.

At the region of second porous membrane 42 aligned to locating point 63 a ligand corresponding to the first soluble antiligand. Binding of the immobile ligand may be by the same methods described with respect to binding of the immobile second antiligand above. For ease of comparison, the shape and orientation of the immobile ligand membrane 42 should be similar to the shape and orientation of the immobile second antiligand.

Figure 4:
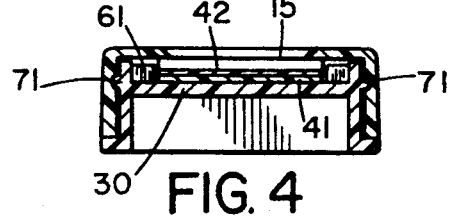
FIG. 4 is a sectional view taken on line 4—4 of FIG. 3.

Thus, when housing cover 5 is placed onto housing floor 20 (preferably by snapping [see, snaps 71 in FIG. 3 and 4] or other suitable coupling means to form snap-tight fit between the two [see, FIGS. 3 and 4]) the soluble first labelled antiligand will be bound beneath or near sample entry port 12, the immobile second unlabelled antiligand will be bound beneath first display port 15 and the immobile ligand will be bound beneath second display port 16.

3. Method: Ligand Assay Procedure

In applying the invention, an analyte sample such as urine which is suspected of containing human chorionic gonadotropin hCG ligand is applied by dropping or pouring (from a pipette or other container) the sample into sample entry port 12 of the assay device described above. No other steps will be taken by the user during the assay; i.e., no washing is required, no addition of a reagent is required and no movement of the device is necessary to obtain visual access to display ports 15 and 16. The user's only next contact with the assay device after the addition of the analyte sample will be to throw the device away when the assay is completed.

Ligands of interest in the analyte sample, if present, will bind by agglutination with the soluble first labelled antiligand on the first porous membrane 40 to form a first conjugate. If desired, further analyte sample may be added up to the maximum binding capacity of unlabelled antiligand and absorbency of the absorbent pad material 43 at the end of the assay. The first conjugates and unbound labelled antiligand, if any, will dissolve into the analyte sample and be carried along therewith by capillary action ("wicking") up to the second porous membrane 42. The position of the first antiligand and first conjugates, if any is indicated as 65 on FIGS. 2, 6 and 7.

All first conjugates carried with the analyte sample fluid will contact the second porous membrane 42. Sample will pass through that second porous membrane 42, bringing the first conjugates, if any, into contact with the second unlabelled antiligand immovably bound to the second porous membrane 70 to bind by agglutination therewith to form second conjugates of labelled antiligand-analyte-unlabelled antiligand. If second conjugates are formed, they will appear as display 66 (FIG. 6).

Analyte sample will continue its migration by wicking through second porous membrane 42 past the immobile second antiligand to the immobile ligand. Labelled first antiligand not conjugated to analyte will bind with the bound immobile ligand to form a third conjugate. The third conjugate will appear as display 67 (FIGS. 6 and 7). Formation of all conjugates in the assay method may be by sandwich or competitive immunoassay techniques well known to those skilled in the art. Within a predetermined time period, any second conjugate present and the third conjugate will undergo a visible color change mediated by the label. In a preferred embodiment, this color change will signal either a positive (analyte present) or negative (analyte not present) reaction by providing two separate reactive zones within those portions of second porous membrane 42 visible to the user through display ports 15 and 16.

Figure 6:
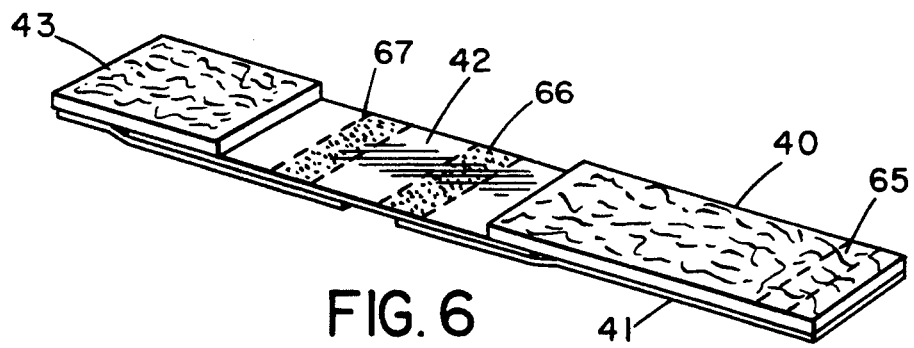
FIG. 6 is a perspective view of the first and second membranes of the assay unit showing a positive assay result.
Figure 7:
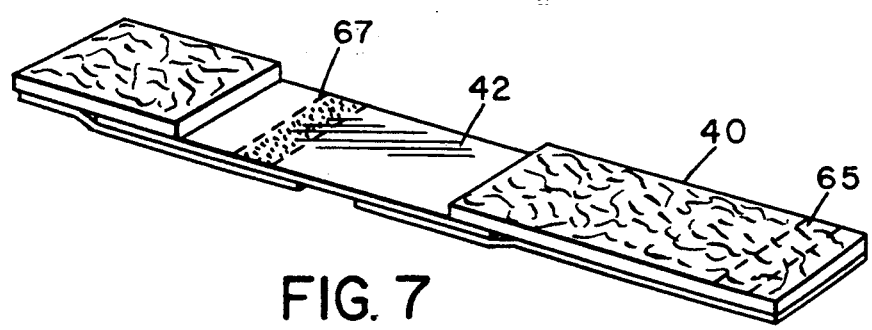
FIG. 7 is a perspective view of the first and second membranes of the assay unit showing a negative assay result.
Figure 8:
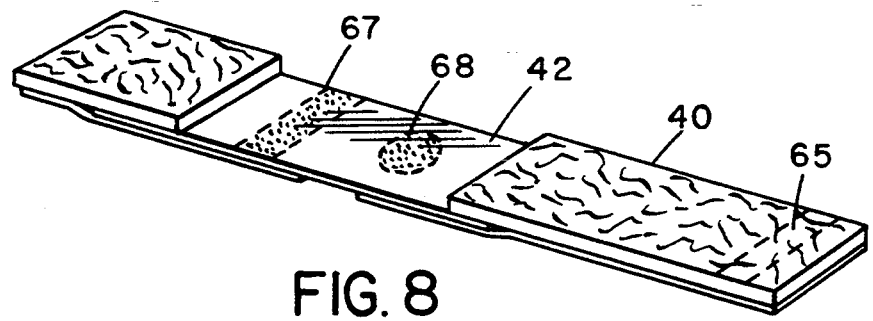
FIG. 8 is a perspective view of the first and second membranes of the assay unit showing an inconclusive assay result.

For example, as shown in FIG. 6, a positive result is indicated when color changes forming substantially similar shapes (in this instance, horizontal bars 66 and 67) appear in both display ports 15 and 16. In contrast, as shown in FIG. 7, a negative result is indicated when a color change forming a distinguishable shape (e.g., a horizontal bar 67) appears only through display port 16. Finally, an inconclusive result is shown in FIG. 8, where color changes appear in both ports having substantially dissimilar shapes (i.e., horizontal bar 67 and smudge 68). In this latter instance, the user would be alerted that the test should be repeated. While due to the decreased impact of leading edge effects and similar phenomena in this assay it is not expected that inconclusive results will be frequent, the assay requires such a small application of analyte sample fluid that repetition should not be problematic in most applications.

Other control or comparative result signals may be provided, including signals which indicate whether an invalid result is obtained, by similar means known to those skilled in the art (see, e.g., the signal system described in European Patent Application No. 8611367.0 [Publication No. 0217 403 A2]).

The following example illustrates a preferred way of using the present invention when it is constructed to include the preferred structure and materials disclosed above. The example is, however, intended only to be illustrative and in no way should be construed to limit the scope of the invention as defined solely by the claims appended hereto. Specifically, it will be appreciated by those skilled in the art that the analyte of interest may be a protein, a peptide, an amino acid, a nucleic acid, a hormone, a steroid, a vitamin, a toxic or other chemical contaminant in the sample fluid, a pathogenic microorganism, and metabolites from analogs of, or antibodies to these substances.

EXAMPLE

This assay procedure is performed using beta-human chorionic gonadotropin (hereinafter "hCG") antibody to form the first conjugate and on anti-hCG-colloidal gold compound to form the second conjugate. The analyte sample is 1 cubic centimeter (hereinafter "cc") of urine suspected of containing HCG; the assay is performed at ambient temperatures not below or exceeding 15°–30° C.

The 1 cc of urine is added to sample entry port 12 by pipette. Within 3 minutes visible color changes (from pure white to pink) through substantially the center of display ports 15 and 16 on second porous membrane 42 are faintly visible. By the end of five minutes, a vividly pink bar symbol has appeared through substantially the center of each display port, indicating the presence of hCG in the sample. All other visible areas of the second porous membrane visible through the second port remain white (the normally visible color of the second porous membrane).

This assay may be performed within 7 days of a suspected conception.

Although the foregoing invention has been described in detail, it will be obvious to those skilled in the art that certain changes and modifications thereto may be made without departing from the scope or spirit of the invention.

We claim:

1. An apparatus for use in assays of fluid samples to detect the presence of one or more ligands of interest therein, comprising:
   (a) a substantially fluid-tight housing having an entry and first and second display ports therein, said entry port for addition of fluid sample to the housing and, said entry and display ports being in fluid communication with one another by means of capillary action through at least one porous membrane, said housing further having a floor divided into two planes, wherein one end of said floor is in a substantially lower but parallel plane to the other end of said floor;
   (b) a slope separating the two planes of the housing floor, wherein the slope is at an angle which is sufficient to slow the passage of fluid sample through the porous membrane;
   (c) a first porous membrane disposed along the lower end of the housing floor in fluid communication with said entry port to which is movably bound a first antiligand complementary to the ligands of interest suspected of existing in the fluid sample, said first antiligand is bound to a label capable of producing a detectable signal indicative of the presence of ligand(s) of interest in the fluid sample;
   (d) a second, porous membrane disposed along the higher end of the housing floor in fluid communication with the first, porous membrane, to which the second, porous membrane is immovably bound:
      (i) one or more second antiligands complementary to the ligands of interest in the fluid sample, said second antiligands being bound beneath said first display port; and
      (ii) first ligands complementary to said first antiligands, said first ligands being bound immovably beneath said second display port;
   (e) one or more fluid gulleys in the higher end of the housing floor to capture excess sample fluid from the second, porous membrane; and
   (f) an absorbent means in fluid communication with said second porous membrane for capturing excess fluid sample from said second porous membrane.

2. The apparatus according to claim 1, wherein said first antiligand is a monoclonal antibody.

3. The apparatus according to claim 2, wherein the monoclonal antibody is specific for human chorionic gonadotropin.

4. The apparatus according to claim 1, wherein said one or more second antiligands are monoclonal antibodies.

5. The apparatus according to claim 4, wherein the monoclonal antibodies are specific for human chorionic gonadotropin.

6. The apparatus according to claim 1, wherein said first antiligand is a polyclonal antibody.

7. The apparatus according to claim 6, wherein the polyclonal antibody is specific for human chorionic gonadotropin.

8. The apparatus according to claim 1, wherein said one or more second antiligands are polyclonal antibodies.

9. The apparatus of claim 8, wherein said polyclonal antibodies are specific for human chorionic gonadotropin.

10. The apparatus according to claim 1 wherein the housing is formed of two sections, the first section forming a top cover through which the ports are disposed, the second section forming a bottom having a depression lying beneath said entry port and a platform lying beneath said display ports formed therein, which platform lies in a horizontal plane above the horizontal plane of said depression, and wherein said top cover fits over the bottom floor so as to seal the container to leakage.

11. The apparatus according to claim 10 wherein the second, porous membrane is attached by adhesive means to said platform.

12. The apparatus according to claim 1 wherein the first, bibulous membrane is of fiberglass.

13. The apparatus according to claim 1 wherein the absorbent means comprises a pad disposed on top of one end of the second, porous membrane.

14. The apparatus of claim 1, wherein the label bound to said first antiligand is a metal label.

15. The apparatus according to claim 14, wherein said metal label is dry form colloidal gold.

16. The apparatus according to claim 1, wherein said label is selected from the group consisting of fluorescers and enzymes.

17. An assay method for the detection of ligands of interest in a fluid sample, comprising the steps of:
  a) adding said fluid sample to the apparatus according to claim 1 through the entry port of said apparatus,
  b) allowing said fluid sample to migrate past the first and second display ports of said apparatus, and
  c) comparing any color change mediated by said label or absence thereof displayed through said first display port to the color change mediated by said label displayed through said second display port to determine if the display visible through said first port is identical to or different from the display visible through said second port, wherein an identical color change in the first and second display ports indicates the presence of analyte, a color change in the second display port and no color change in the first display indicates no analyte, and different color changes in the first and second display ports indicates a compromised assay.

18. An apparatus according to claim 1 wherein the second, porous membrane is chromatographic.

* * * * *